United States Patent
Harttig et al.

(10) Patent No.: US 11,324,563 B2
(45) Date of Patent: May 10, 2022

(54) PROTECTIVE COVERINGS FOR HAND-HELD MEDICAL DEVICES

(71) Applicant: Roche Diabetes Care, Inc., Indianapolis, IN (US)

(72) Inventors: Herbert Harttig, Neustadt (DE); Sebastian Liedtke, Heidelberg (DE); Matthias Mock, Basel (CH)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 720 days.

(21) Appl. No.: 14/872,603

(22) Filed: Oct. 1, 2015

(65) Prior Publication Data

US 2016/0022363 A1 Jan. 28, 2016

Related U.S. Application Data

(63) Continuation of application No. PCT/EP2014/057136, filed on Apr. 9, 2014.

(30) Foreign Application Priority Data

Apr. 9, 2013 (EP) .................. 13162924.8

(51) Int. Cl.
*A61B 46/10* (2016.01)
*G01N 21/15* (2006.01)
*G01N 21/84* (2006.01)

(52) U.S. Cl.
CPC ............. *A61B 46/10* (2016.02); *G01N 21/15* (2013.01); *G01N 21/8483* (2013.01)

(58) Field of Classification Search
CPC ....... A61B 46/10; A61B 50/00; A61B 5/1405; A61B 5/1433; A61B 5/145;

(Continued)

(56) References Cited

U.S. PATENT DOCUMENTS 5,490,524 A 2/1996 Williams et al.
5,522,255 A * 6/1996 Neel ...................... G01N 11/06
356/39

(Continued)

FOREIGN PATENT DOCUMENTS

EP       1279365 B1    12/2006
JP       2004313269 A  11/2004
WO       2012116798 A1  9/2012

OTHER PUBLICATIONS

Passage definition. Collins English Dictionary. https://www.collinsdictionary.com/US/dictionary/english/passage. definition 1. (Year: 2019).*

(Continued)

*Primary Examiner* — Tarla R Patel
(74) *Attorney, Agent, or Firm* — Woodard, Emhardt, Henry, Reeves & Wagner, LLP

(57) ABSTRACT

Protective coverings are provided for hand-held medical devices that have a measuring port for a disposable analytical test element. The coverings also include a sleeve having a reception opening and can be slipped over the devices to at least partially enclose the devices in a usable protected state. The coverings further include a test element adapter formed as an integral part of the sleeve to receive the test element in alignment with a measuring port, where the sleeve includes the test element adapter and is arranged as a sealing barrier between the test element and the device port in a protected state.

20 Claims, 4 Drawing Sheets

(58) Field of Classification Search
CPC .............. A61B 5/14532; A61B 5/1455; A61B 2562/0295; A61B 2562/24; A61B 2562/242; A61B 2562/247; A61B 2050/0052; A61B 2050/0053; A61B 2050/0065; A61B 2050/0067; A61B 2050/0069; A61B 2050/008; A61B 2050/0083; A61B 2050/0085; A61B 46/00; A61B 46/23; A46B 2560/0431; A61H 2230/202; B01L 3/5027; G01N 21/15; G01N 21/8483; G01N 27/307; G01N 33/4875; G01N 33/48757; G01N 33/48778; G01N 33/66

See application file for complete search history.

(56) References Cited

U.S. PATENT DOCUMENTS

| | | | | |
|---|---|---|---|---|
| 5,526,120 | A * | 6/1996 | Jina | G01N 21/8483 356/446 |
| 5,714,123 | A * | 2/1998 | Sohrab | G01N 33/52 422/560 |
| 5,872,713 | A * | 2/1999 | Douglas | A61B 5/415 702/85 |
| 6,979,571 | B2 * | 12/2005 | Modzelewski | G01N 21/8483 422/562 |
| 7,850,664 | B1 | 12/2010 | Pruter | |
| 2006/0222567 | A1 * | 10/2006 | Kloepfer | G01N 21/8483 422/68.1 |
| 2010/0311090 | A1 * | 12/2010 | Bae | A61B 5/14546 435/11 |
| 2011/0089175 | A1 | 4/2011 | Modin et al. | |
| 2012/0100601 | A1 * | 4/2012 | Simmons | G01N 33/48785 435/287.7 |
| 2012/0221064 | A1 * | 8/2012 | Wooldridge | A61B 46/10 607/2 |
| 2013/0048530 | A1 * | 2/2013 | Yang | A61B 10/0045 206/524.1 |

OTHER PUBLICATIONS

Sealing definition, Merriam Webster Online Dictionary, p. 2 definition 2a, https://www.merriam-webster.com/dictionary/sealing (Year: 2020).*

Barrier definition, Merriam Webster Online Dictionary, p. 2 definition 1a, https://www.merriam-webster.com/dictionary/barrier (Year: 2020).*

* cited by examiner

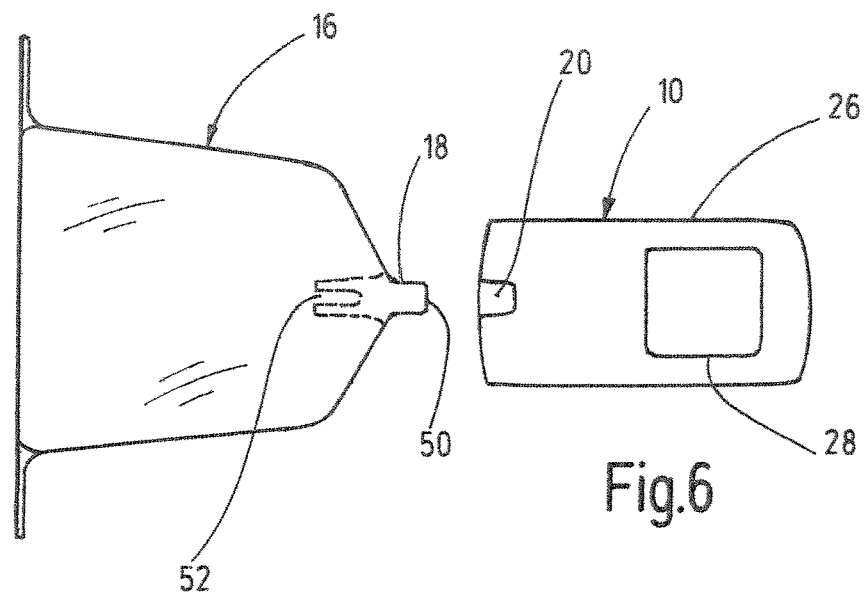
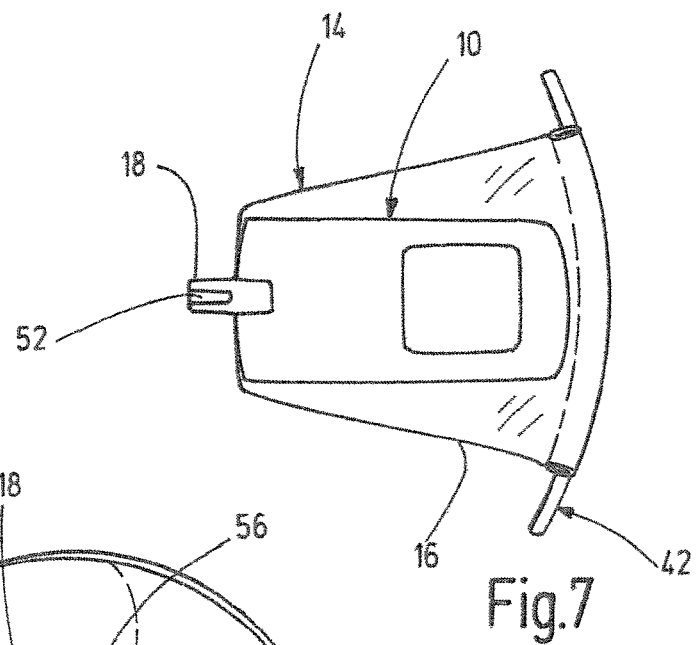
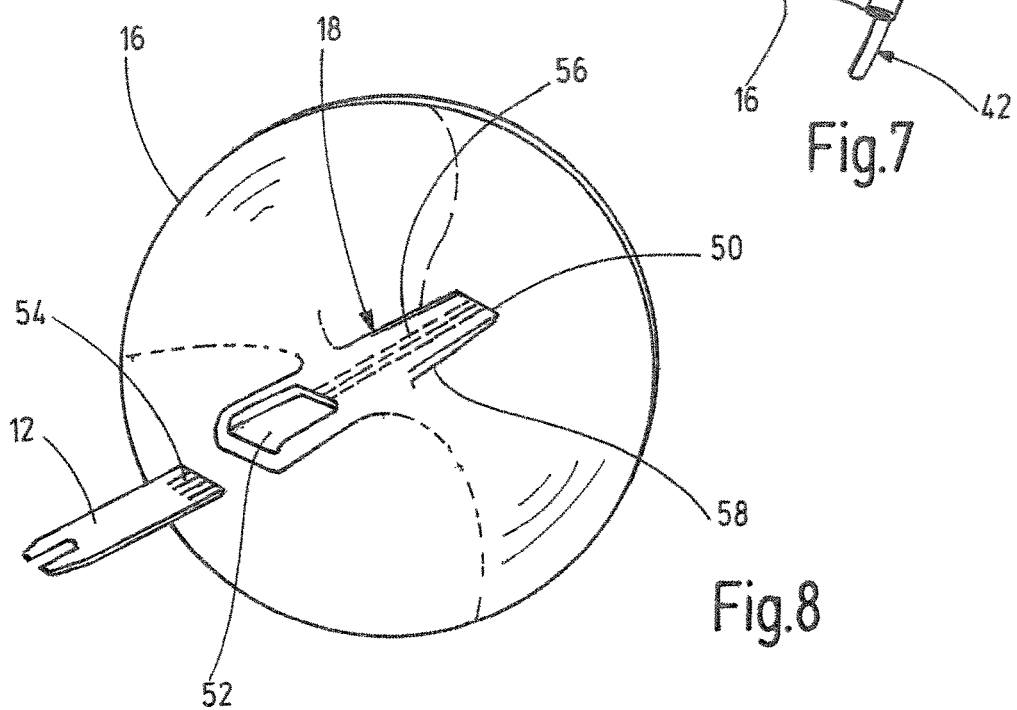

PROTECTIVE COVERINGS FOR HAND-HELD MEDICAL DEVICES

CROSS-REFERENCE TO RELATED APPLICATIONS

This patent application is a continuation of Int'l Patent Application No. PCT/EP2014/057136 (filed 9 Apr. 2014), which claims priority to and the benefit of EP Patent Application No. 13162924.8 (filed 9 Apr. 2013). Each patent application is incorporated herein by reference as if set forth in its entirety.

TECHNICAL FIELD

This patent application relates generally to medical diagnostics and engineering, and more particularly, it relates to protective coverings for hand-held medical devices that have a measuring port for a disposable analytical test element to which a sample can be applied, where the coverings include a sleeve having a reception opening and can be mounted on the devices to partially or fully enclose the devices in a usable protected state.

BACKGROUND

Int'l Patent Application Publication No. WO 2012/116798 discloses a protective barrier for medical devices. The protective barrier includes a casing having a plurality of perforations, where the casing is separable along the perforations to remove medical devices after use. The medical devices include a test element receiving port that is aligned with an open passage of the casing, allowing insertion of the test element through casing and into the receiving port. With such a configuration, it is intended to avoid or minimize using disinfectants when removing contamination while preventing contamination during use of the medical devices so they can be re-used at a later time.

On this basis, there is a need in the art for improved protective barriers having improved efficiency for safe and reliable use of hand-held medical devices in patient proximity.

BRIEF SUMMARY

An inventive concept described herein includes avoiding contaminating handheld medical devices, especially in the area of a sample measuring interface. Correspondingly, this inventive concept is achieved by a protective covering for such devices that partially or fully enclose them in a usable protected state. This inventive concept can be incorporated into exemplary protective coverings as described herein and in more detail below.

For example, protective coverings/sheaths for hand-held medical devices are provided that include a sleeve having a reception opening and that can be mounted on the devices to partially or fully enclose them in a usable protected state, where the hand-held medical devices also include a measuring port for a disposable analytical test element to which a body fluid sample can be applied. The protective coverings also include a test element adapter formed as an integral part of the sleeve to receive the test element in alignment with the measuring port, where the sleeve, including the test element adapter, is arranged as a sealing barrier between the test element and the measuring port in a protected state.

To provide for a precise alignment for test elements that can be inserted into a test element adapter by a user, it is advantageous when the test element adapter has holding elements to engage and hold the test element in a defined position relative to the measuring port.

In some instances, the test element adapter can be detachably connected to the hand-held medical devices via guiding, latching or plug-in elements. In other instances, the test element adapter has an optical window to establish a sealed optical measuring path between the test element and the measuring port, where the optical window can be a transparent material such as, for example, polyethylene terephthalate (PET), poly(methyl methacrylate) (PMMA), polycarbonate (PC), polycarbonate acrylonitrile-butadiene-styrene (PC-ABS), polystyrene (PS), styrene acrylonitrile (SAN) or acrylonitrile styrene acrylate (ASA).

In some instances, the test element is an electrochemical test element and the test element adapter has an electrical connector to provide a galvanic coupling between the test element and the measuring port of the device. It is advantageous when the electrical connector includes a female connector part on an outside of the sleeve to insert the test element and a male connector part on an inside of the sleeve that can be plugged-in into the measuring port of the device.

To reduce constructional expenditure, the electrical connector can include conducting elements formed from metal, especially at least partly a noble metal, organic conductors or carbon derivatives, contained in a non-conducting matrix.

A safeguard improvement can be achieved by a closure to close the reception opening for the device after the sleeve is slipped over the device. In some instances, it is advantageous when the closure is construed as a hook-and-pile (Velcro®) or foil slide-locking or foil folding fastener.

To sanitarily enclose the device, it is advantageous when the sleeve has a first closed end, and when the closure provides a second closed end, such that the device is fully protected against the environment.

Alternatively, the sleeve can be a flexible, unshaped or shapeless member that can be fitted to the shape of the devices, such that the sleeve is conformed or adopted to a 3-dimensional (3D) design of the devices. In this context, the sleeve also can include a flexible foil material that can be elastically adapted to an outer contour of the devices.

With regard to design and usability of the devices, it is advantageous when the sleeve is transparent at least in an area covering a display or a control unit of the devices so that the usual handling is not affected.

In some instances, the sleeve includes first and second sleeve parts that can be connected by adherence in an overlapping joint region, such that the devices are fully enclosed in the combined sleeve.

To simplify application, it is advantageous when the sleeve includes a sack-like part that can be turned inside-out or everted over the test element adapter when mounted onto the devices.

Likewise, and to simplify removal, it is advantageous when the sleeve includes tear-off parts in a multi-layered arrangement that can be successively detached from the devices for sequential use. In this arrangement, it is conceivable that the sleeve is designed as a disposable and is discarded after consumption of all tear-off parts.

In some instances, the sleeve is sterile and forms an aseptic shielding for the devices.

In view of the foregoing, hand-held medical devices also are provided that include a measuring port for a disposable analytical test element and a protective covering as outlined above.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIGS. 6 and 7 are a top view of a third exemplary protective covering in an initial and an assembled state.

FIG. 8 is an expanded view of a test element adapter of the covering of FIGS. 6 and 7.

Corresponding reference characters indicate corresponding parts throughout the several views of the drawings.

Figure 1:
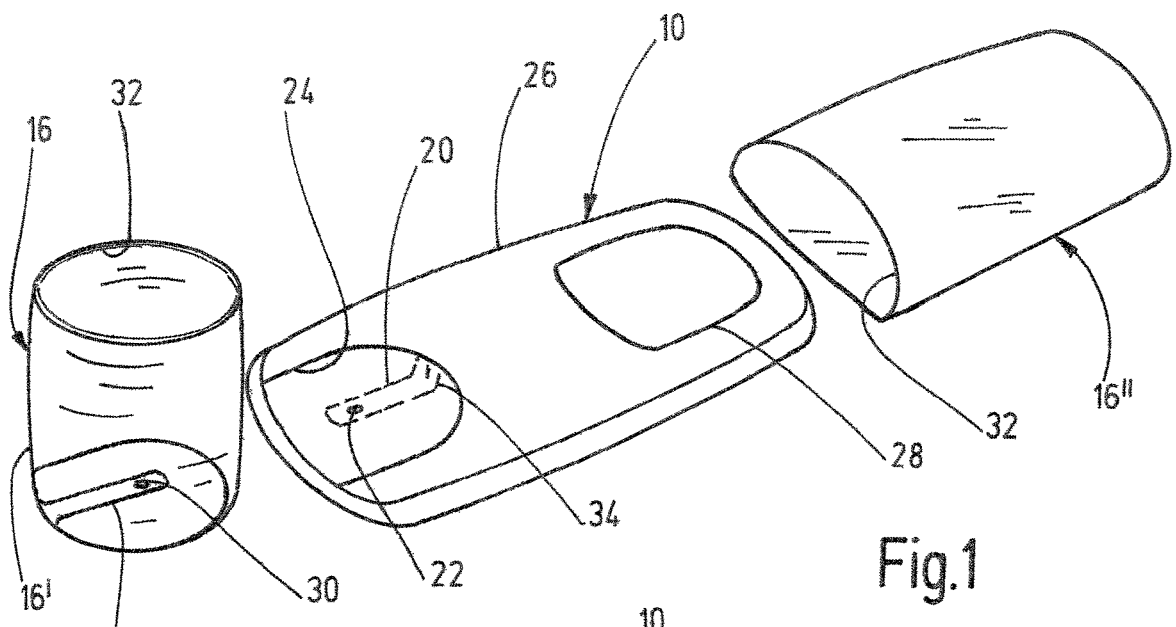
FIG. 1 is a perspective, exploded view of a blood glucose meter and an exemplary protective covering in an initial state.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The protective coverings/sleeves now will be described more fully hereinafter with reference to the accompanying drawings, in which some, but not all embodiments of the inventive concept are shown. Indeed, the protective coverings may be embodied in many different forms and should not be construed as limited to the embodiments set forth herein; rather, these embodiments are provided so that this disclosure will satisfy applicable legal requirements.

Likewise, many modifications and other embodiments of the protective coverings described herein will come to mind to one of skill in the art to which the disclosure pertains having the benefit of the teachings presented in the foregoing descriptions and the associated drawings. Therefore, it is to be understood that the protective coverings are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the protective coverings, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Protective coverings/sleeves for medical devices such as analyte test meters are described herein. The medical devices generally include a test element adapter formed as an integral part of the coverings described herein to receive a test element in alignment with a device port, where the coverings include the test element adapter is arranged as a sealing barrier between the test element and the device port in the protected state. In this manner, the coverings herein fulfill multiple functions, namely, as a protective sleeve and as an adapter replicating an instrument port. Due to these measures, direct contact can be prevented between a fluid sample and instrument parts. This is important where disposable test elements to which body fluid samples can be applied are handled by patients having impaired physical conditions, so that an accurate positioning cannot be guaranteed. Such measurements may include the direct application of fresh blood sampled from a body part (e.g., for blood coagulation or glucose measurements). Specifically in a medical environment, the function as a sealed barrier can reduce the spread of infectious material, both when the devices are carried into or out of such an environment. In this connection, it is advantageous when such devices are fully enclosed in the sleeve using, for example, a sealing technology. Alternatively it is possible that the devices can be inserted into the sleeve through a reception opening and only partly enclosed therein.

Protective Coverings/Sleeves

The drawings show an arrangement of a medical device configured as a portable blood glucose meter 10 for processing of disposable analytical test elements 12, such as test strips, and a protective covering 14 including a one- or two-part sleeve 16 that can be mounted on the meter 10 and an integrated test element adapter 18 for inserting a test element 12 in the assembled state.

As shown in FIG. 1, the meter 10 has a measuring port 20 to which the test element adapter 18 can be aligned. The measuring port 20 is intended for optical measurements on a test element 12 and includes a transparent inset 22 closely embedded in a tray 24 of the device housing 26. The transparent inset 22 is arranged in the optical path of a reflectometric measuring device of the meter 10 for a reflectance measurement on a separate test element 12 loaded with a blood sample, where the result can be obtained on the spot and shown to the user via display 28. Such glucose measurements are known per se to one of skill in the art and need not to be explained in further detail.

To provide a sealing barrier between the measuring port 20 and the test element 12, the sleeve 16 can be slipped over the device housing 26 and mounted such that an optical window 30 of the test element adapter 18 is aligned with the transparent inset 22 of the housing 26. For this purpose, both parts 16', 16" of the sleeve 16 have an opening 32 for receiving or being imposed on opposed portions of the elongate housing 26. To ensure a tight sealing, the sleeve 16 consists of a flexible foil material that can be elastically adapted to an outer contour of the housing 26 and can be transparent at least in an area covering the display 28.

The alignment of the optical window 30 with the transparent inset 22 can be facilitated by means of guiding or latching elements 34 to which the test element adapter 18 can be detachably connected. In the assembled state, the optical window 30 should closely adhere to the transparent inset 22, such that air gaps are avoided and losses in the optical path are minimized. For further improvement in this regard, the optical window 30 includes a transparent material selected from, for example, PET, PMMA, PC, PC-ABS, PS, SAN or ASA.

Figure 2:
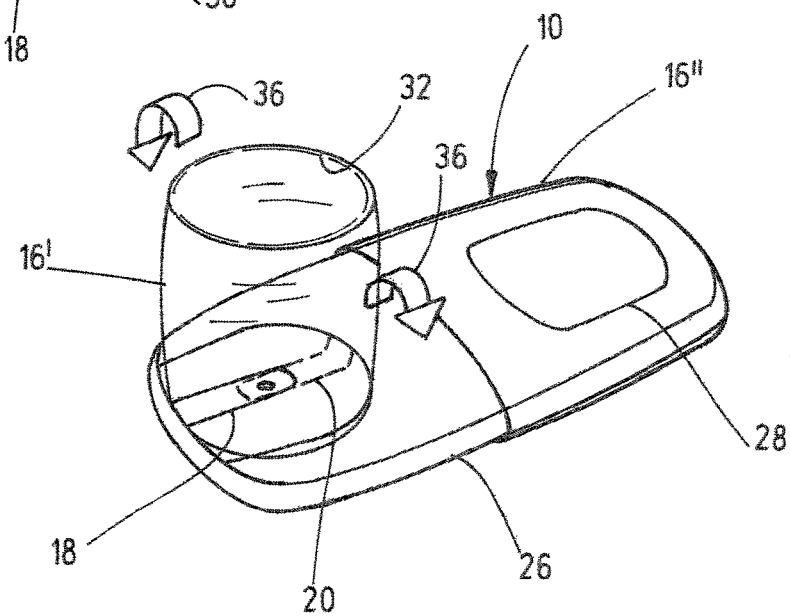
FIG. 2 shows a partly assembled state of the covering on the meter of FIG. 1.

FIG. 2 further shows an assembly of sleeve 16 on the device 10. Opening 32 of the sleeve part 16" is sized to allow the device 10 to be inserted therethrough, so that at least a first half of housing 26 including the display 28 is hermetically sealed. Then, the test element adapter 18 is connected to the measuring port 20, and sleeve part 16' is slipped over the second half of housing 26. Here, the flexibility of the foil material allows the user to extend and evert the sack-like sleeve part 16' in direction of arrows 36.

Figure 3:
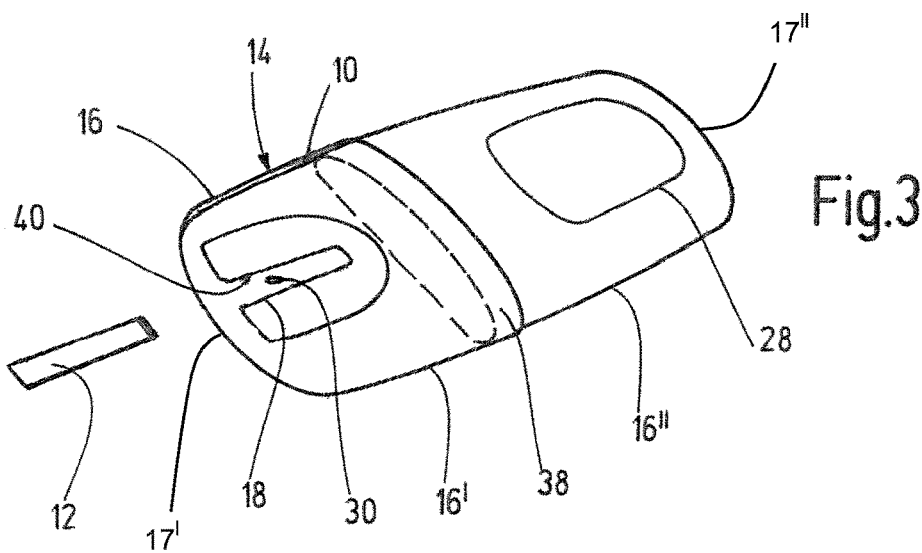
FIG. 3 shows the meter inside the covering in a protected state ready for use of a test strip.

FIG. 3 shows the completely mounted state, in which the sleeve parts 16', 16" are connected by adherence in an overlapping joint region 38, such that the device 10 is fully enclosed in the combined sleeve 16. The sleeve parts 16', 16" respectively have a first closed end 17', and a second closed end 17", such that the meter 10 is completely encased. Purposefully, the sleeve 16 including the integrated test element adapter 18 is sterilized to form an aseptic protective covering 14. In the protected state, the test element 12 can be connected to test element adapter 18 without direct contact to the meter 10. Test element adapter 18 includes holding elements 40 to engage and hold the test element 12 in a defined position relative to the measuring window 30 in alignment with the measuring port 20.

If wanted, the user can tear off and discard the covering 14 as an expendable item. It also is conceivable that the sleeve 16 includes tear-off parts 16' in a multi-layered arrangement that can be successively detached from the 10 device for sequential use.

Figure 4:
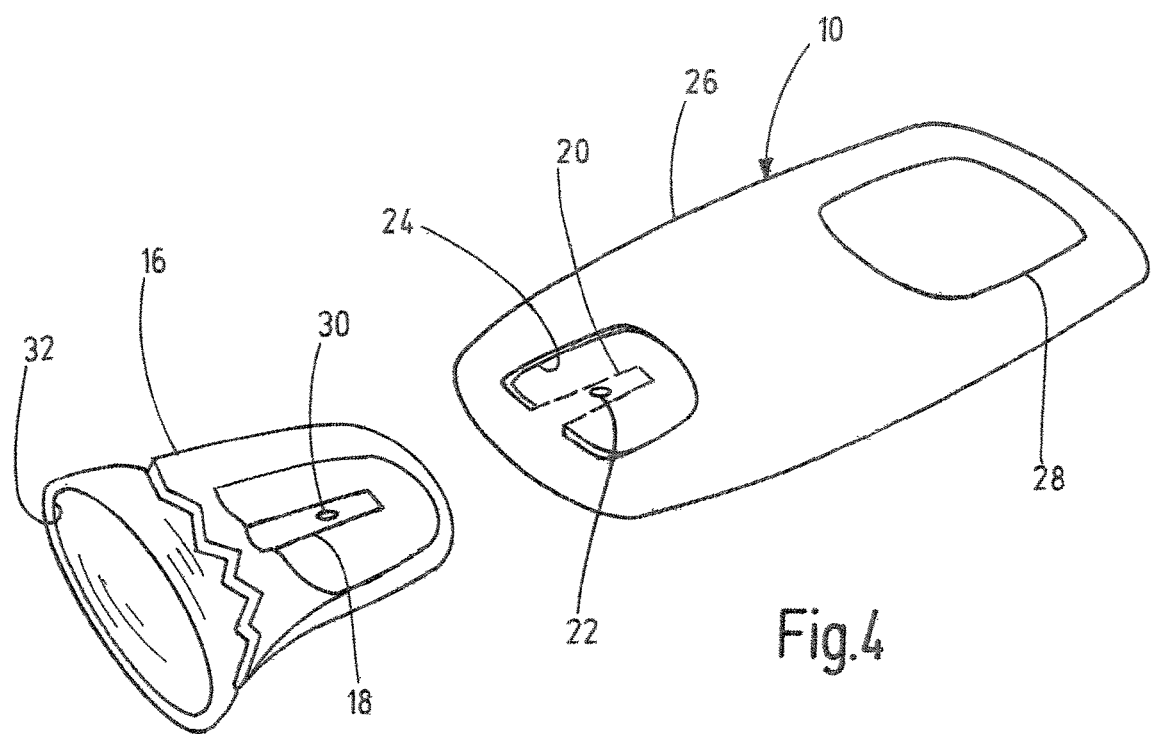
FIG. 4 is a perspective, exploded view of another exemplary protective covering in the form of a one-piece covering.
Figure 5:
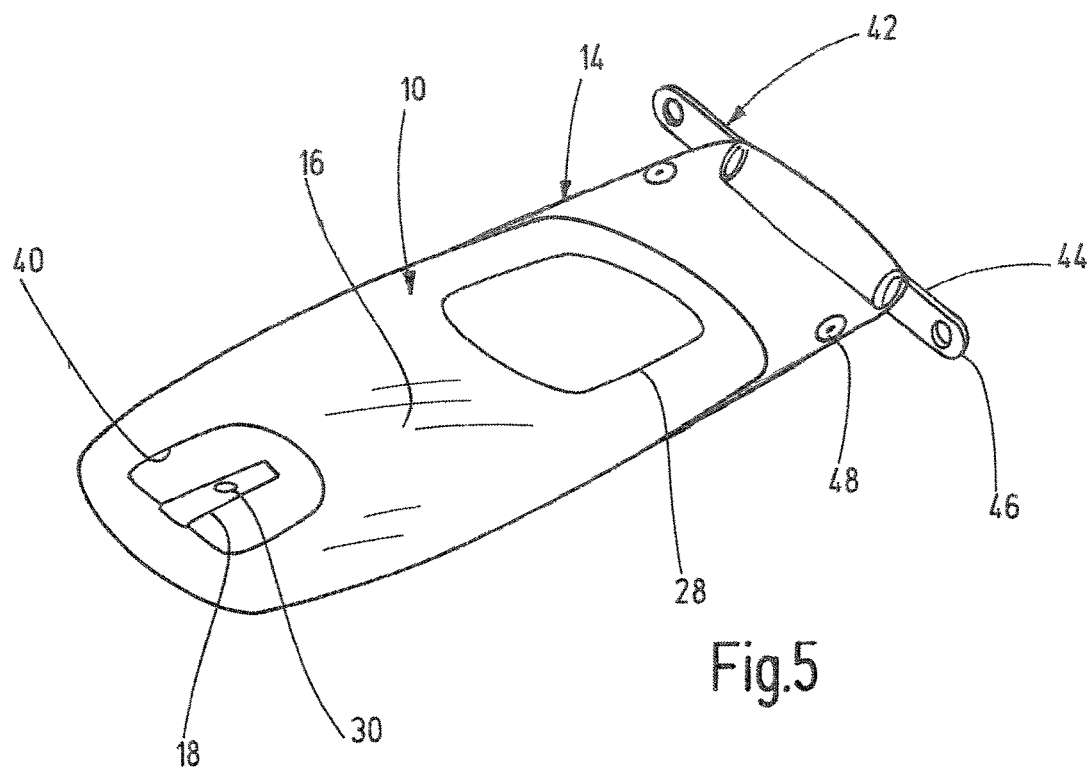
FIG. 5 shows an assembled state of the exemplary covering of FIG. 4.

FIGS. 4 and 5 show an alternative protective covering including a one-part sleeve 16. Here, similar elements have like reference numerals as previously described. As distinguished to the previously described covering, the one-part sleeve 16 can be completely slipped over the device 10, such that housing 28 is entirely received. Thereafter, a closure 42 is used to close the reception opening 32 in the overlaying end section of the sleeve 16. The closure 42 is construed as a foil folding fastener 44 that has end flaps 46 that can be snapped on pressure locks 48 on the sleeve 16.

FIGS. 6 to 8 show a glucometer 10 with a measuring port 20 that is intended for electrochemical measurements on a test element 12. For this purpose, the measuring port 20 is constructed as a female connector that has contact springs for a wired connection to an amperometric measuring device of the meter 10 (not shown). A single-part sleeve 16 is provided with an integrated electrical test element adapter 18. As shown in FIG. 7, the sleeve 16 can be slipped over the device 10 and closed by means of a foil folding fastener 44 as previously described.

As shown in FIG. 8, the test element adapter 18 has a distal male connector end 50 that can be plugged into the measuring port 20 and a proximal female connector end 52 that can receive the contact section 54 of test element 12. The male end 50 is designed similar to the contact section 54, whereas the female end 52 replicates the measuring port 20. In this way, it also is conceivable that the measuring port 20 receives a test element 12 for a measurement in an unprotected state when the protective covering 14 is removed.

In the protected state, when the meter 10 is hermetically enclosed in the covering 14, the test element adapter 18 forms an electrical connector to provide a galvanic coupling between the test element 12 and the measuring port 20 of the device 10. Conducting paths 56 are formed within the test element adapter 18 from metal, such as at least partly a noble metal, organic conductors or carbon derivatives, contained in the non-conducting matrix of a carrier 58.

The test element adapter 18 may allow an automatic switch-on function of the device 10 when a test element 12 is inserted.

In case of electrochemical measurements, a corresponding change in resistivity can be detected through the conducting paths 56, and a monitoring circuit of the device can be operable for a turn-on procedure.

Figure 9:
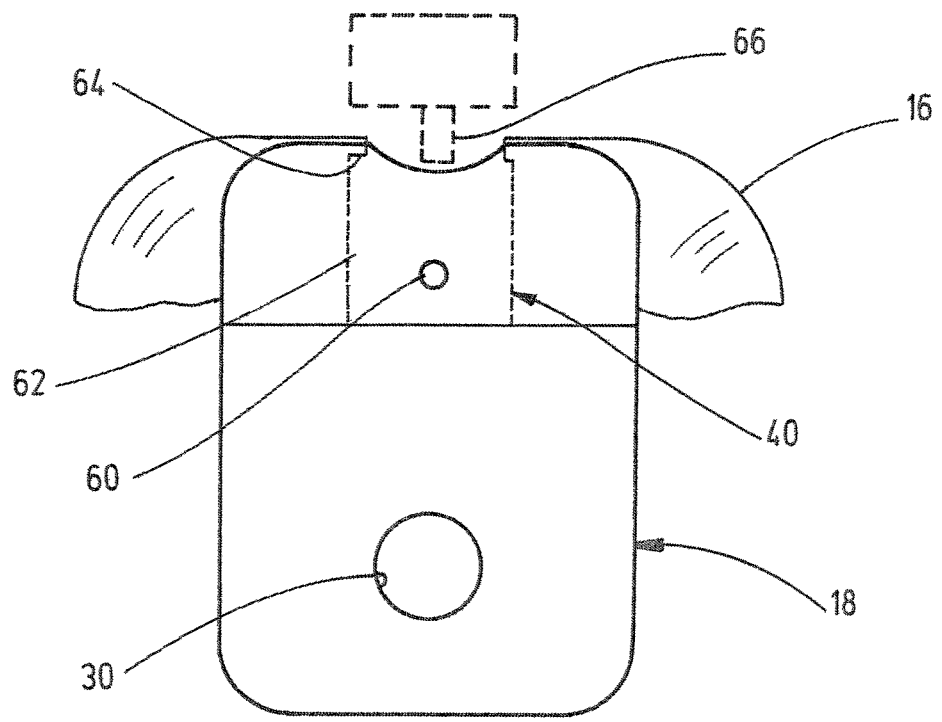
FIG. 9 is a sectional top view of a sleeve including a test element adapter for optical measurements.

FIG. 9 shows an exemplary test element adapter 18 providing a similar switch-on function for optically working systems. The adapter 18 includes holding elements 40 formed as a pin 60 and a holding-down clamp 62 for a form-locking engagement of an inserted test element 12. Then, the distal end of the test element abuts the stop edges 64 and at the same time actuates a micro-switch 66 on the side of the device 10 to effectuate power-on.

Correspondingly, an additional aspect of the disclosure is a protective covering 14 that includes a sleeve 16 that can be slipped over a device 10 and that includes a test element adapter 18, where the test element adapter 18 is operable to provide a switch-on function of the device 10 when a test element 12 is inserted into the test element adapter 18.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

Listing of Reference Numbers 10 blood glucose meter
12 analytical test element 14 protective covering
16 one- or two-part sleeve
18 test element adapter
20 measuring port
22 transparent inset
24 tray
26 device housing
28 display
30 optical window
32 opening
34 guiding or latching elements
36 direction
38 overlapping joint region
40 holding elements
42 closure
44 fastener
46 end flaps
48 pressure locks
50 male connector end
52 female connector end
54 contact section
56 conducting paths
58 carrier
60 pin
62 holding-down clamp
64 stop edges
66 micro-switch

The invention claimed is:

1. A protective covering for a hand-held medical device that has a first test element port configured for receiving an insertion end of a test element in a measuring position for measuring an analyte, the covering comprising:
a sleeve comprising a reception opening sized to receive the medical device, wherein the sleeve can be mounted on the hand-held medical device to partially or fully enclose the hand-held medical device in a usable protected state; and
a test element adapter formed as an integral part of the sleeve and including a second test element port configured to receive the test element, the test element adapter further comprising an insertion end configured to be received by the first test element port, the test element adapter positioning the test element in the measuring position within the first test element port when the insertion end of the test element adapter is received within the test element port, the test element adapter preventing direct contact between the insertion end of the test element and the first test element port of the medical device when the test element is received within the test element adapter.

2. The protective covering of claim 1, wherein the test element can be inserted into the test element adapter by a user, and wherein the test element adapter comprises holding elements to engage and hold the test element in a defined position relative to the second test element port.

3. The protective covering of claim 1, wherein the test element adapter can be detachably connected to the medical device via guiding or latching or plug-in elements.

4. The protective covering of claim 1, wherein the first test element port is for electrochemical measurements on a test element and the test element is an electrochemical test element, the test element adapter comprising at least one electrical connector to provide a galvanic coupling between a test element received within the second test element port and the first test element port.

5. The protective covering of claim 4, wherein the at least one electrical connector comprises conducting elements formed at least partly from metal selected from the group consisting of a noble metal, organic conductors and carbon derivatives, contained in a nonconducting matrix.

6. The protective covering of claim 1, further comprising a closure to close the reception opening for the hand-held medical device when the sleeve is slipped over the hand-held medical device.

7. The protective covering of claim 6, wherein the sleeve provides a first closed end and the closure provides a second closed end, such that the hand-held medical device is fully protected against the environment.

8. The protective covering of claim 1, wherein the sleeve is a flexible foil material that can be elastically adapted to an outer contour of the hand-held medical device.

9. The protective covering of claim 1, wherein the sleeve is transparent at least in an area covering a display of the hand-held medical device.

10. The protective covering of claim 1, wherein the sleeve comprises first and second sleeve parts that form a combined sleeve and that can be connected by adherence in an overlapping joint region, such that the hand-held medical device is fully enclosed in the combined sleeve.

11. The protective covering of claim 10, wherein each of the sleeve parts comprises a hermetically sealed closed end.

12. The protective covering of claim 1, wherein the sleeve comprises tear-off parts in a multi-layered arrangement that can be successively detached from the hand-held medical device for sequential use.

13. The protective covering of claim 1, wherein the sleeve is sterile and forms an aseptic shielding for the hand-held medical device.

14. The protective covering of claim 1, wherein the test element adapter provides an automatic switch-on function of the hand-held medical device when a test element is inserted.

15. The protective covering of claim 1, wherein the hand-held medical device includes a transparent inset in an optical path of a measuring device of the hand-held medical device, the test element adapter including an optical window being aligned with the transparent inset when the test element adapter is received within the first test element port.

16. The protective covering of claim 1, wherein the test element adapter includes a male connector part adapted to be received within the first test element port of the hand-held medical device and a female connector part adapted to receive therein a test element, a test element received within the second test element port being in a measurement position when the male connector part is received within the first test element port.

17. A protective covering for a hand-held medical device that has a first test element port configured for receiving an insertion end of a test element in a measuring position for measuring an analyte, wherein the covering comprises:
a sleeve comprising a reception opening sized to receive the medical device, wherein the sleeve can be mounted on the hand-held medical device to partially or fully enclose the hand-held medical device in a usable protected state; and
a test element adapter formed as an integral part of the sleeve and including a second test element port adapted to receive the test element,
the test element adapter comprising an insertion end configured to be received in the measuring position by the first test element port of the medical device, the test element adapter preventing direct contact between the insertion end of the test element and the first test element port of the medical device when the test element is received in the measuring position within the second test element port, the test element adapter further comprising an optical window positioned to establish an optical measuring path between the test element and the first test element port when the test element is contained within the test element adapter and the insertion end of the test element adapter is received in the measuring position within the first test element port.

18. The protective covering of claim 17, wherein the optical window comprises a transparent material selected from the group consisting of polyethylene terephthalate (PET), polymethyl methacrylate (PMMA), polycarbonate (PC), polycarbonate acrylonitrile-butadiene-styrene (PC-ABS), polystyrene (PS), styrene acrylonitrile (SAN) and acrylonitrile styrene acrylate (ASA).

19. The protective covering of claim 4, wherein the at least one electrical connector comprises a female connector part adapted to receive the test element and a male connector part adapted to be received in the first test element port.

20. A protective covering for a hand-held medical device that has a first test element port configured for receiving an insertion end of a test element in a measuring position for measuring an analyte, the covering comprising:
 a sleeve comprising a reception opening sized to receive the medical device, wherein the sleeve can be mounted on the hand-held medical device to partially or fully enclose the hand-held medical device in a usable protected state; and
 a test element adapter formed as an integral part of the sleeve and having a distal portion received within the first test element port, the test element being received within the test element adapter, the test element including an insertion end received within the distal portion of the test element adapter, the test element being in a measurement position within the second test element port when the test element adapter is received within the first test element port, the distal portion of the test element adapter preventing direct contact between the insertion end of the test element and the medical device.

* * * * *